(12) United States Patent
Stork

(10) Patent No.: US 6,291,734 B1
(45) Date of Patent: Sep. 18, 2001

(54) INTEGRATED LOW PRESSURE DEPROPANIZER/DEBUTANIZER COLUMN

(75) Inventor: Karl Stork, Houston, TX (US)

(73) Assignee: Kellogg Brown & Root, Inc., Houston, TX (US)

( * ) Notice: Subject to any disclaimer, the term of this patent is extended or adjusted under 35 U.S.C. 154(b) by 0 days.

(21) Appl. No.: 09/334,319

(22) Filed: Jun. 16, 1999

(51) Int. Cl.[7] .................. C07C 7/04; C10G 7/00; B01D 3/14
(52) U.S. Cl. .............. 585/809; 208/347; 208/351; 208/363; 202/158; 169/111
(58) Field of Search ..................... 208/347, 351, 208/363; 585/809; 196/111; 202/158

(56) References Cited

U.S. PATENT DOCUMENTS

| | | |
|---|---|---|
| 4,411,676 * | 10/1983 | Tedder .................................. 62/24 |
| 5,678,424 | 10/1997 | Nazar . |
| 5,709,780 | 1/1998 | Ognisty et al. . |
| 5,755,933 | 5/1998 | Ognisty et al. . |
| 5,884,504 | 3/1999 | Nazar . |

* cited by examiner

*Primary Examiner*—Walter D. Griffin
*Assistant Examiner*—Tam M. Nguyen
(74) *Attorney, Agent, or Firm*—Kellogg Brown & Root, Inc.

(57) ABSTRACT

An integrated debutanizer and low pressure depropanizer column and process for separating a feed stream comprising $C_3$'s, $C_4$'s and $C_5+$ is disclosed. A single shell houses a refluxed upper portion and a lower portion of the column. A generally vertical wall partitions the lower portion of the column into a debutanizer section and a depropanizer stripper section. The upper column portion is used as the absorption section of the depropanizer. The feed is supplied to an intermediate stage in the debutanizer, and the debutanizer is operated at a lower pressure (and correspondingly lower temperature) matching that of the low pressure depropanizer. The design allows the use of one slightly larger column in place of the two large columns previously used for separate debutanization and low pressure depropanization.

16 Claims, 8 Drawing Sheets

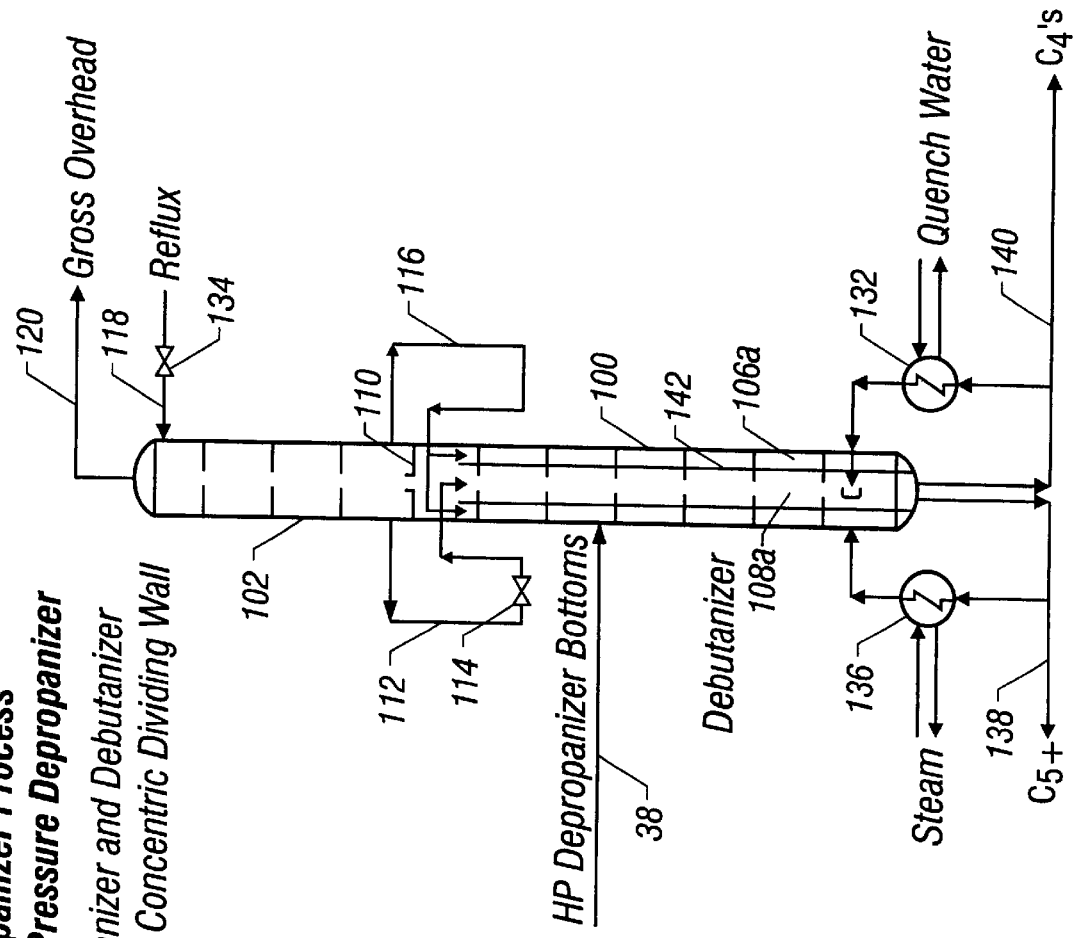

INTEGRATED LOW PRESSURE DEPROPANIZER/DEBUTANIZER COLUMN

FIELD OF THE INVENTION

The present invention relates to an apparatus and method for the depropanization and debutanization in an olefin plant processing propane and heavier feedstocks, and particularly to the use of an integrated column which combines both the low pressure depropanizer and debutanizer into a single column.

BACKGROUND OF THE INVENTION

A typical process for the separation and recovery of olefins from pyrolysis furnaces operated with feedstocks heavier than ethane, is known as the front end depropanizer and front end acetylene hydrogenation scheme. A brief review of the typical front end depropanizer process is in order.

Starting with the separation section 2 after the water quench, as shown on the simplified process flow diagram of FIG. 1, there are three stages 4,6,8 of conventional compression to raise the pressure of the process gas from just above atmospheric to a pressure of about 15 bars (210 psia). Condensed liquids, i.e. hydrocarbons and water, are separated.

The gas is then treated in a conventional two or three stage caustic wash tower 10 as shown in FIG. 2 for the removal of carbon dioxide and hydrogen sulfide. The gas is cooled and mildly chilled before entering the dryers 12,14. Water is removed completely.

The gas is then further chilled in propylene refrigerant exchanger 16 seen in FIG. 3, and enters the high pressure depropanizer 18 which does not really operate at high pressure but is only called that because there is also a low pressure depropanizer 20. The high pressure depropanizer 18 typically operates at a pressure of 12 bars (170 psia), and the low pressure depropanizer 20 at a pressure of 8.5 bars (120 psia).

The overhead of the high pressure depropanizer 18 is usually compressed in compressor 22 to a pressure of 38 bars (550 psia) and is then sent to the acetylene hydrogenation system 24 which typically consists of two or three adiabatic reactors in series with inter-cooler for the removal of the heat of reaction. The reactor effluent is cooled in cooling water exchanger 26 and partially condensed in propylene refrigerant exchanger 28. A portion of the condensate is used as reflux via line 30 for the high pressure depropanizer 18. The rest is sent to the demethanizer stripper 32 (see FIG. 4) via line 34.

In the stripping section 36 of the high pressure depropanizer 18 only ethane and lighter components are removed, resulting in a fairly low bottoms temperature of 56° C. (133° F.). The bottoms product is sent via line 38 to the low pressure depropanizer 20 where it is separated into $C_3$'s and $C_{4+}$. The $C_3$ is used as reflux in the high pressure depropanizer 18 via line 30, while the $C_{4+}$ is sent to the debutanizer 86 via line 40. Due to the low operating pressure, the bottoms temperatures in the depropanizers 18,20 are quite low, namely 56° C. (133° F.) and 71° C. (160° F.). Therefore, there is no fouling in either tower 18,20 or their respective reboilers 42,44.

Debutanizer 86 separates the $C_{4+}$ stream via line 40 into overhead vapor stream 85 comprising $C_4$'s and bottoms stream 88 comprising $C_{5+}$. The debutanizer 86 is heated with 2.2 bar steam in reboiler 90. Overhead vapor is condensed in condenser 92 with cooling water. Condensate is refluxed to the debutanizer 86 via line 94 and valve 96. A $C_4$ product stream is recovered via line 98.

The acetylene hydrogenation unit 24 is highly efficient and selective. The acetylene removal easily results in acetylene concentrations of less than 1 ppm in the final ethylene product while the ethylene gain amounts to 50% or more of the acetylene. Due to the high hydrogen content of the feed gas, no carbonaceous material is deposited on the catalyst. The catalyst needs no regeneration and thus the reactors 24 need no spares. Green oil formation is miniscule.

In the acetylene hydrogenation reactor 24 about 80% of the methyl-acetylene and 20% of the propadiene are converted to propylene. If the olefins plant produces polymer grade propylene the remaining $C_3H_4$ can be easily fractionated into the propane product; the high conversion of methyl-acetylene and propadiene in the acetylene hydrogenation reactors obviates the need for an additional separate $C_3H_4$ hydrogenation system.

The operational stability of the acetylene hydrogenation reactor 24 is enhanced by its location in the gross overhead loop of the depropanizer 18 and in the minimum flow recycle circuit of the fourth stage of compression 22. These factors reduce the acetylene concentration in the inlet to the reactor 24 and stabilize the flow rate irrespective of the furnace throughput.

The vapor and liquid from the reflux accumulator 46 of the high pressure depropanizer 18 flow to the chilling and demethanization section 48 (see FIG. 4). The liquid plus the condensate formed at −37° C. (−35° F.) is sent via respective lines 34 and 50 to the demethanizer stripper 32. The overhead vapor from the demethanizer stripper 32 plus the liquids formed at lower temperatures are sent to the main demethanizer 52 via respective lines 54 and 56. The tower 52 is reboiled by reboiler 58 with condensing propylene refrigerant, and reflux is condensed in heat exchanger 60 with low temperature ethylene refrigerant.

The respective bottoms products 62,64 of the two demethanizers 32,52, after some heat exchange which is not shown, enter the prior art deethanizer 66. The tower 66 recovers approximately 40 percent of the ethylene contained in the two feeds as high purity product. Sixty percent of the ethylene and all the ethane leave the tower 66 as a side stream 68 and proceed to the ethylene fractionator 70. The deethanizer 66 is reboiled by reboiler 74 with quench water and reflux is condensed in exchanger 76 with −40° propylene refrigerant. The bottoms product 72 of the deethanizer 66 is a stream containing propylene, propane and the remaining $C_3H_4$. It flows to a conventional propylene fractionator (not shown). Because of the ethylene fractionation in its top section 78, the deethanizer 66 has fifty more trays than a conventional deethanizer (without the side draw) which produces a mixed ethylene and ethane overhead product in line 80.

The ethylene fractionator 70 is a relatively low pressure tower typically operating at 4 bars (60 psia) with approximately 100 trays. It uses an open heat pump. Ethylene refrigerant is condensed in the reboiler 82 and is then used as reflux via line 84. Effectively, the reboiler 82 also serves as the reflux condenser. There are no reflux pumps and there is no reflux drum.

Another possible deethanizer/ethylene fractionator arrangement is disclosed in U.S. Pat. Nos. 5,678,424 and 5,884,504 both to Nazar which are hereby incorporated herein by reference.

A deethanizer and ethylene fractionator integrated into a single column is disclosed in my earlier U.S. Ser. No.

09/266,214 filed Mar. 10, 1999, which is hereby incorporated by reference for purposes of U.S. patent practice.

Other references of interest are U.S. Pat. Nos. 5,709,780 and 5,755,933, both to Ognisty et al.

SUMMARY OF THE INVENTION

The present invention combines the low pressure depropanizer and debutanizer of the prior art into a single fractionation column, reduces the pressure of the low pressure depropanizer to that of the debutanizer and locates the debutanizer and the stripping section of the low pressure depropanizer in the bottom portion of a single distillation column divided by a vertical wall. Locating the debutanizer and the stripping section of the low pressure depropanizer in the bottom section of a single distillation column divided by a vertical wall has the capital cost savings of replacing two large columns with a slightly larger column; eliminates the debutanizer reflux condenser, drum and pumps; and employs a much smaller debutanizer reboiler.

In one aspect, the present invention provides an integrated low pressure depropanizer and debutanizer column for separating a feed stream comprising $C_3$'S, $C_4$'s and $C_5$'s into a $C_3$'S stream, a $C_4$'S stream and a $C_{5+}$ stream. The integrated column is made of a single shell housing a refluxed upper portion and a lower portion. Each of the integrated column portions comprise multiple vapor-liquid contacting elements. A generally vertical wall partitions the lower portion into a debutanizer section and a depropanizer stripper section. A feed line supplies at least one feed stream to at least one feed stage of the debutanizer section of the lower portion of the column, between a plurality of absorption stages above the feed stage and a plurality of stripping stages below the feed stage, for producing an overhead vapor stream from the low pressure debutanizer section consisting essentially of $C_3$'s and $C_4$'s and a bottoms stream consisting essentially of $C_5$ and heavier components. A distribution pan with vapor chimney(s) at the lower end of the upper portion of the column facilitates passage of vapors from the debutanizer and depropanizer stripper sections into the upper column portion, and collects liquid for passage from the upper portion of the column into the upper stage of the debutanizer section and into the depropanizer stripping section.

The integrated column can have from 40 to 60 trays in the depropanizer and a low pressure debutanizer section comprising from 25 to 45 trays. The upper and lower portions of the integrated column preferably have the same cross-sectional diameter. The integrated column can also include a reboiler for the debutanizer section heated with steam or some other suitable heating medium. The integrated column can also include a reboiler for the depropanizer stripper section, heated by quench water. The integrated column preferably includes a line for refluxing the upper portion of the column with the $C_3$'s. The integrated column preferably comprises respective liquid lines from the distribution pan to the tops of the debutanizer section and the depropanizer stripper section. The line from the distribution pan to the top of the debutanizer section can include a valve for controlling the amount of liquid supplied to the low pressure debutanizer section. The integrated column preferably has an operating pressure of from 1.5 to 12 bars (20 to 180 psia).

In another aspect, the invention provides a process for separating a feed stream comprising $C_3$'S, $C_4$'S and $C_{5+}$ into a $C_3$'S stream, a $C_4$'s stream and a $C_{5+}$ stream. The method includes supplying the feed stream to the at least one feed stage of the debutanizer section of the lower portion of the integrated column described above; passing overhead vapor from the debutanizer and depropanizer stripper sections through the chimney(s) of the distribution pan to the upper portion of the column; refluxing the upper portion of the column with $C_3$'s and recovering $C_3$'s essentially free of $C_4$'S overhead from the upper portion of the column; passing liquid from the distribution pan into an upper stage of the debutanizer section and into an upper stage of the depropanizer stripper section; reboiling the debutanizer section and recovering a $C_{5+}$ bottoms product stream therefrom essentially free of $C_3$'s and $C_4$'s; and reboiling the depropanizer stripper section and recovering a $C_4$'s bottoms product stream therefrom essentially free of $C_3$'s and $C_{5+}$.

The debutanizer section preferably comprises from 25 to 45 trays, and the upper and lower portions of the integrated column have the same cross-sectional diameter. The process can include controlling the amount of liquid feed to the upper stage of the debutanizer section from the distribution pan. The integrated column can be operated at a pressure from 1.5 to 12 bars (20 to 180 psia). The debutanizer section is preferably reboiled with steam.

BRIEF DESCRIPTION OF THE DRAWINGS

FIG. 8 is a simplified process flow diagram of $C_3$'s/$C_4$'s recovery in a front end depropanizer process according to an alternate embodiment of the present invention.

DETAILED DESCRIPTION OF THE INVENTION

Figure 1:
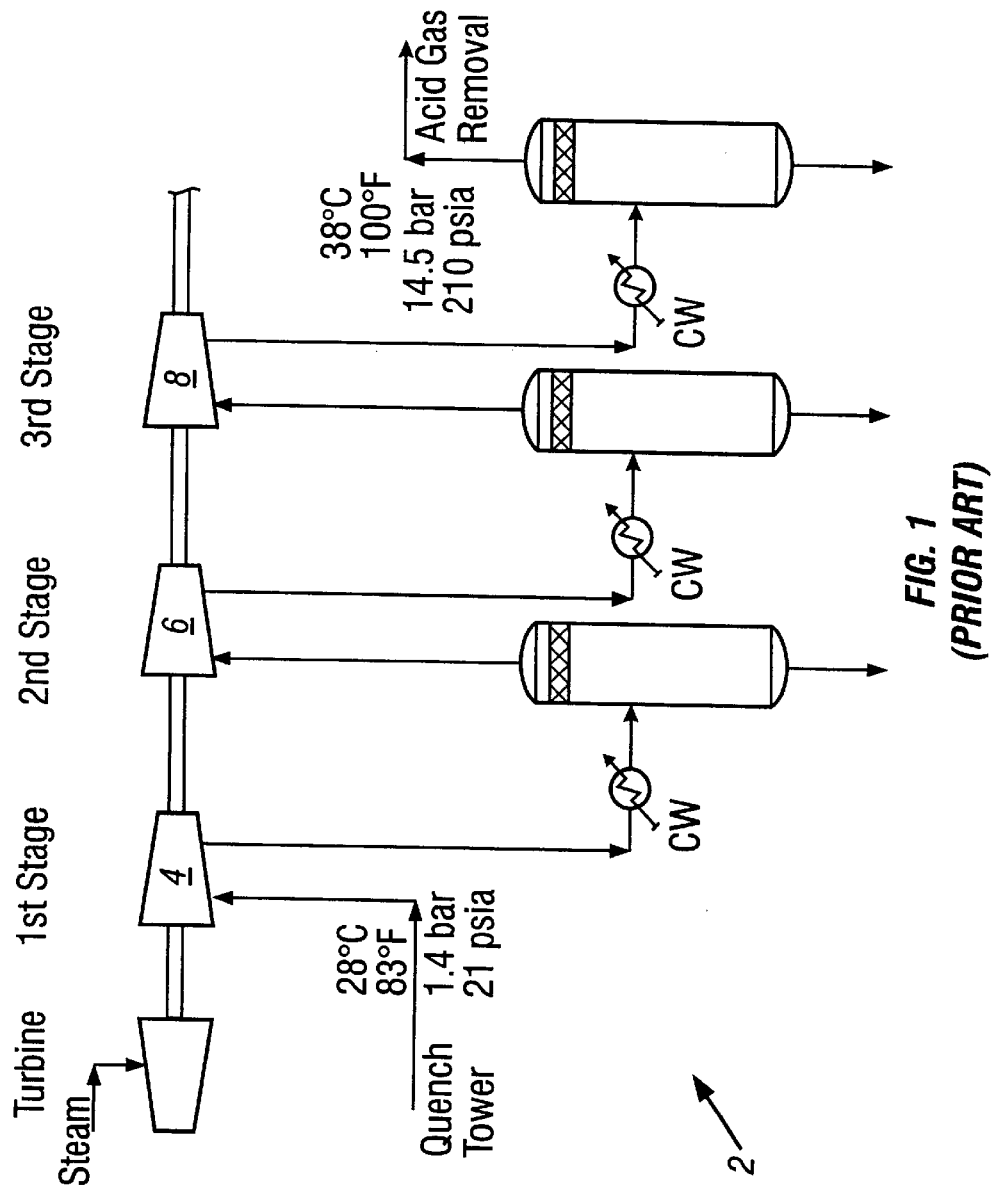
FIG. 1 (prior art) is a simplified process flow diagram showing the three stages of wet process gas compression in a front end depropanizer process.
Figure 2:
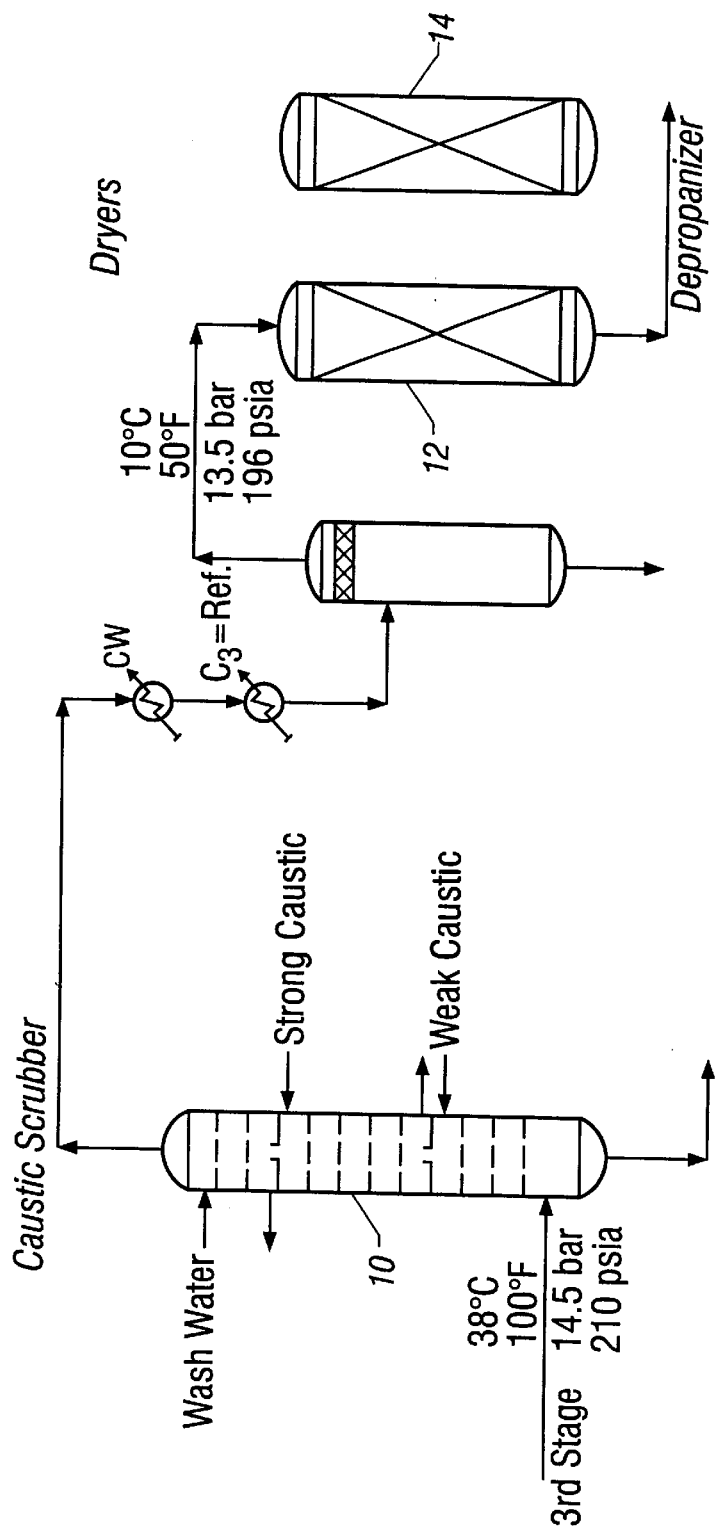
FIG. 2 (prior art) is a simplified flow diagram of acid gas removal and drying in a front end depropanizer process.
Figure 3:
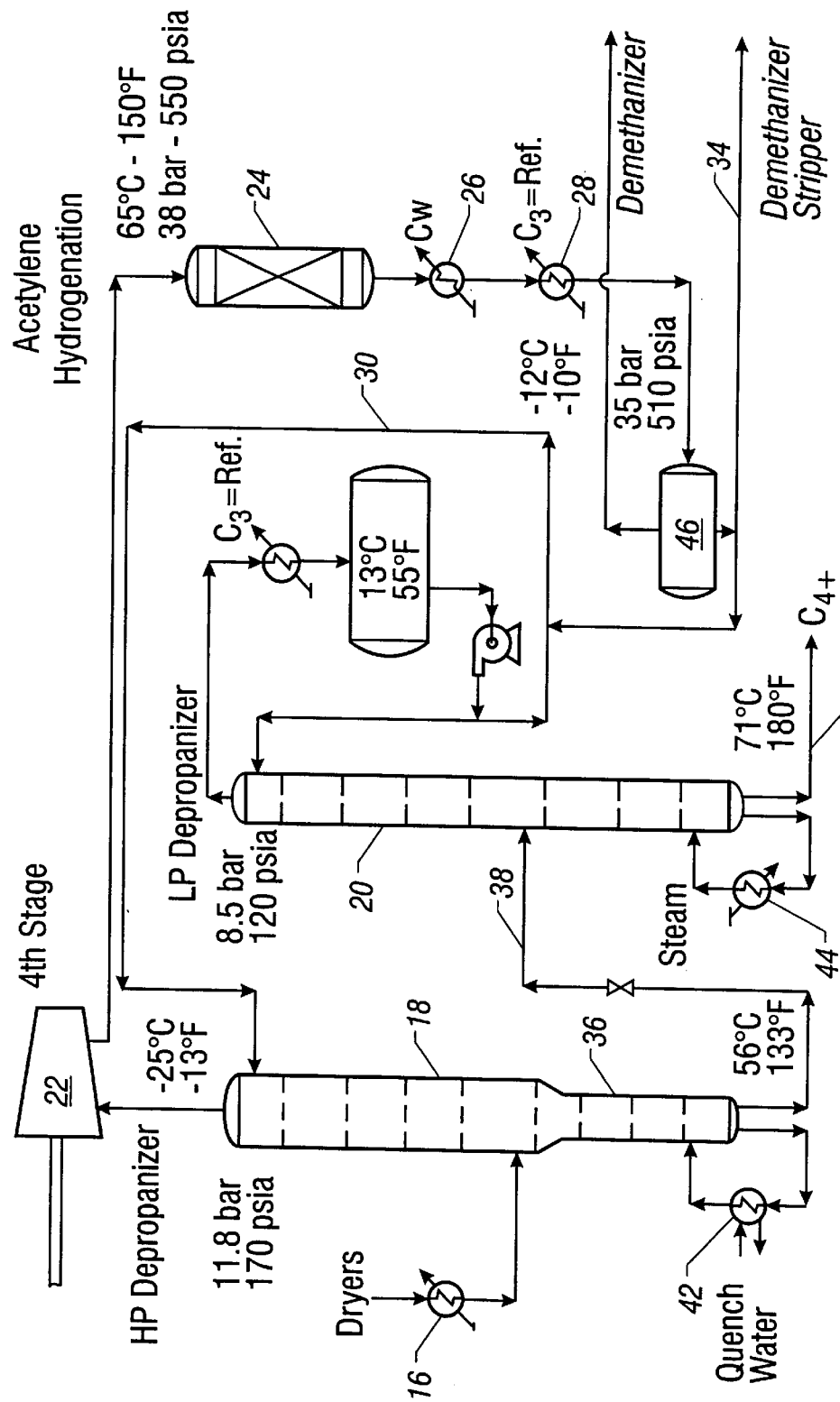
FIG. 3 (prior art) is a simplified process flow diagram of fourth stage compression and high pressure/low pressure depropanizers in a front end depropanizer process.
Figure 4:
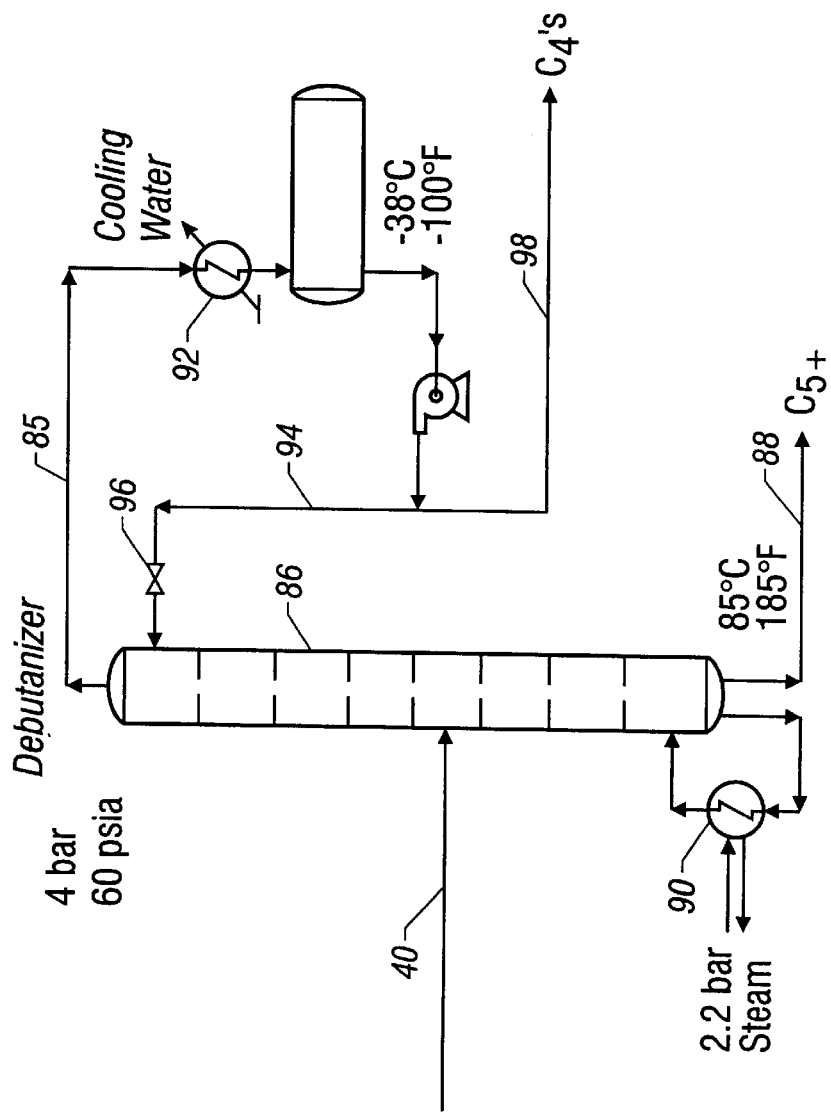
FIG. 4 (prior art) is a simplified flow diagram of a debutanizer in a front end depropanizer process.
Figure 5:
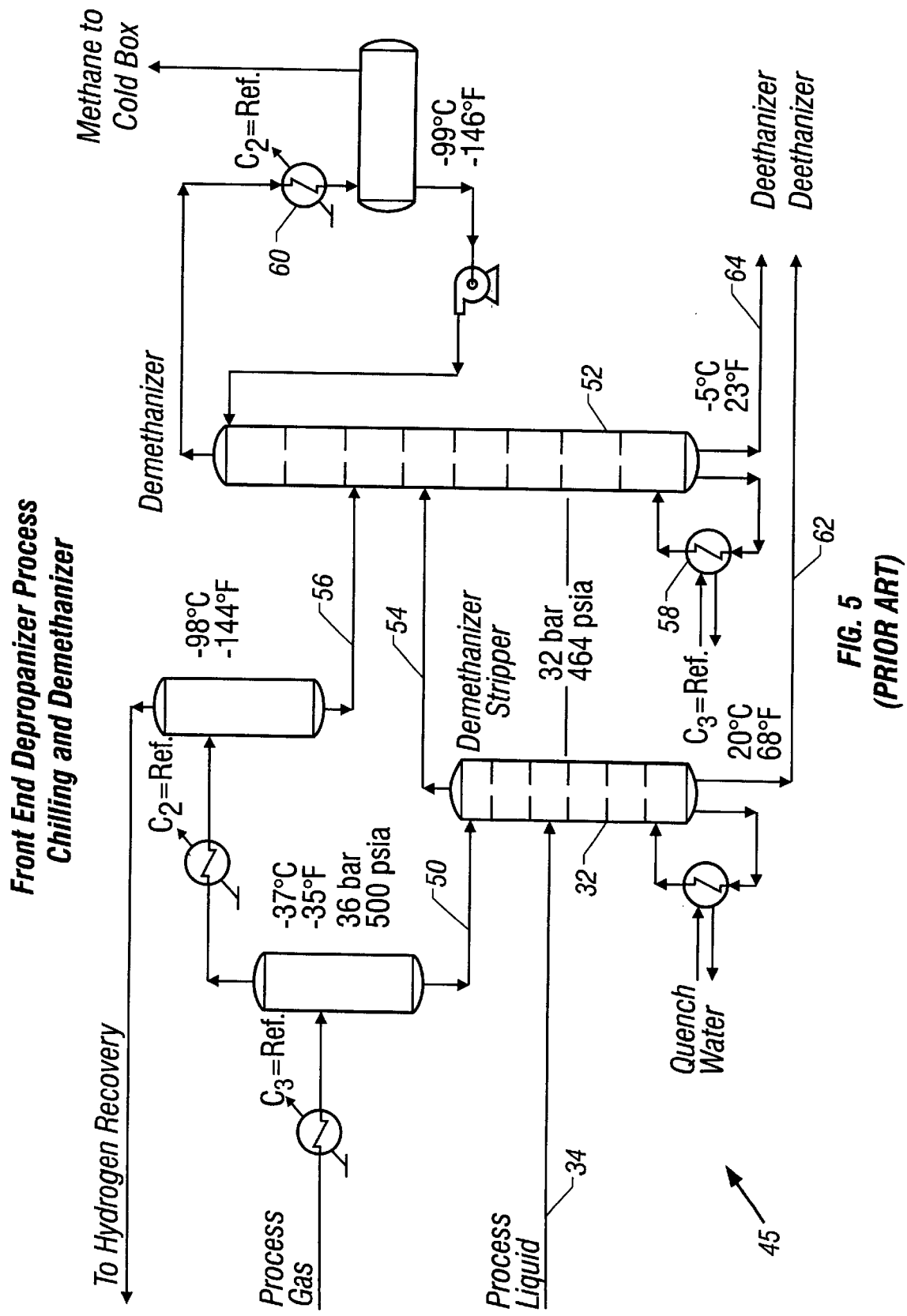
FIG. 5 (prior art) is a simplified process flow diagram of a demethanizer stripper and demethanizer in a front end depropanizer process.
Figure 6:
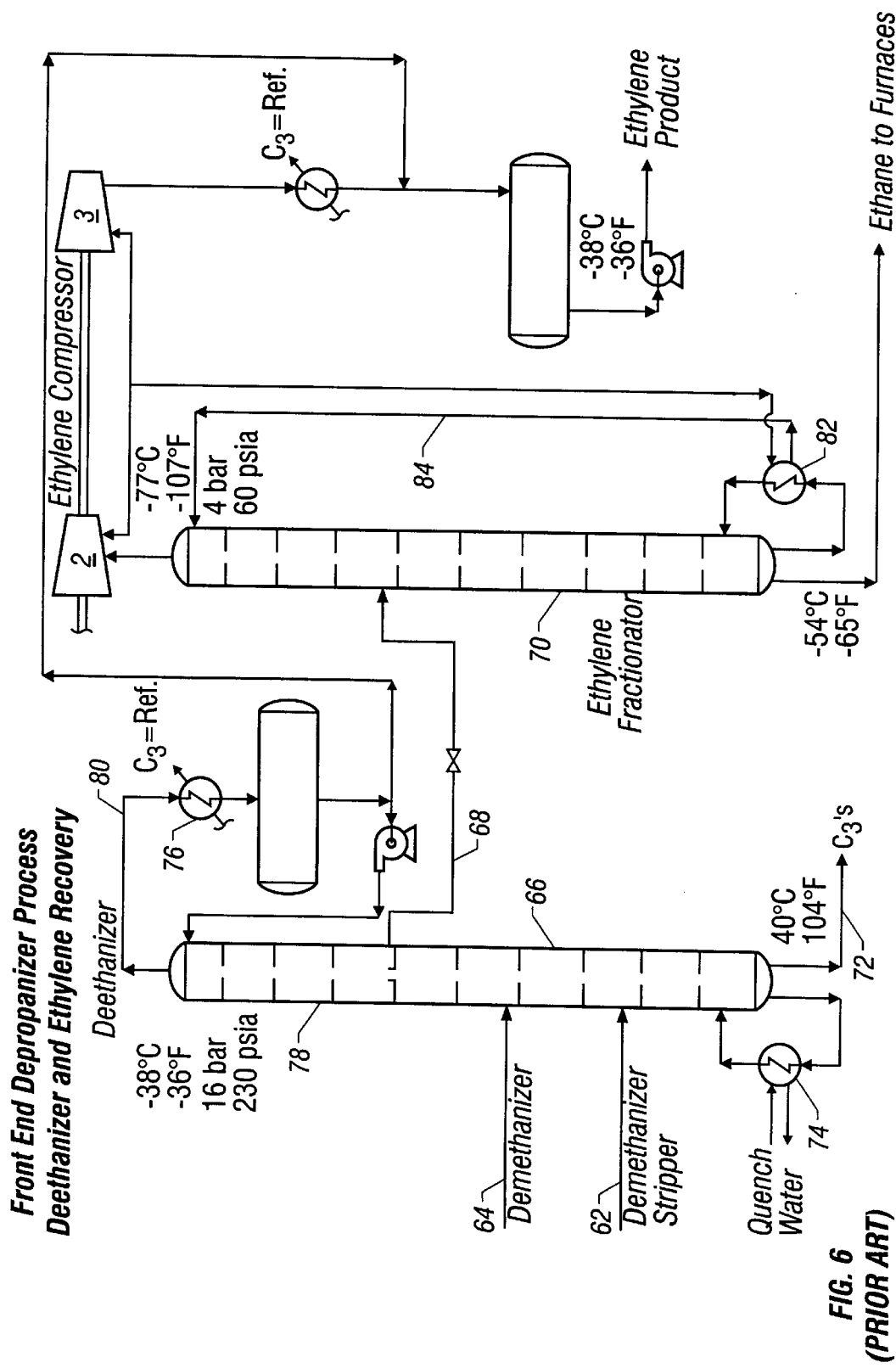
FIG. 6 (prior art) is a simplified flow diagram of a conventional deethanizer and ethylene fractionator in a front end depropanizer process.
Figure 7:
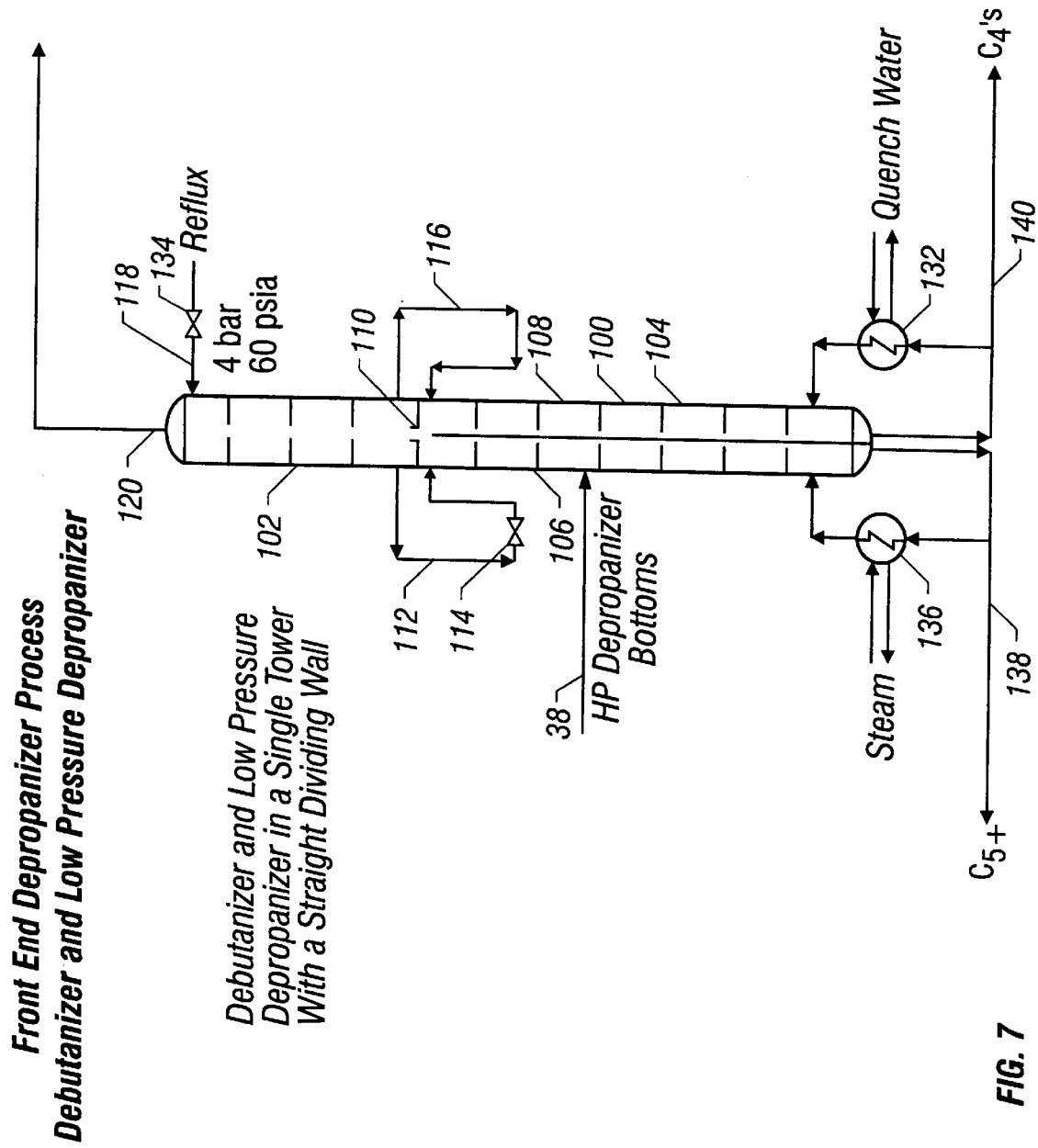
FIG. 7 is a simplified process flow diagram of $C_3$'s/$C_4$'s recovery in a front end depropanizer process according to one embodiment of the present invention.

With reference to FIG. 7, a single tower 100 achieves the sharp separation of high purity $C_3$'s as an overhead product, a mixed $C_{5+}$ product with an extremely low $C_3/C_4$ content as a bottoms product on the left side 106, and a $C_4$'s product on the right side 108 of the lower portion 104 of the column 100. The column 100 is preferably operated at a pressure of from 1.5 to 12 bars (20 to 180 psia), more preferably at a pressure of from 2 to 6 bars (30 to 90 psia), and especially at about 4 bars (60 psia).

The column 100 includes an upper portion 102 and the lower portion 104. The upper portion 102 serves as the absorption section of the low pressure depropanizer. The lower section 104 of the column is partitioned by a vertical partition which divides the lower portion 104 into left and right sides 106,108, respectively. The left side 106 serves as the low pressure debutanizer, whereas the right side 108 serves as the stripping section of the depropanizer.

The high pressure depropanizer bottoms 38 are fed to trays or stages in the left section 106 which have about the same composition. Vapors from the left section 106 pass overhead with vapors from the right section 108 through a distribution pan 110 which allows vapor to pass upwardly therethrough, but restrains liquid from passing from the upper column portion 102 into the lower column portion 104. The vapor from the left section 106 can be in fluid communication with the vapor from the right section 108 at the top tray or stage of each section 106,108.

A line 112 introduces liquid from the distribution pan 110 to the top stage of the left section 106. The line 112 can include a control valve 114 for controlling the rate of liquid reflux to the left section 106. A line 116 is used to introduce liquid from the distribution pan 110 to the top of right section 108. Typically the amount of reflux in line 112 is controlled via valve 114, while the line 116 is a liquid overflow from the distribution pan 110. The amount of liquid in line 112 is usually a fraction of the liquid in line 116.

The upper portion 102 of the column 100 is refluxed with $C_3$'s via line 118. Essentially pure $C_3$'s vapor is recovered overhead in line 120. Reboiler 132 is furnished with quench water which supplies heat to a lower end of the right section 108. The reboiler 132 can be external or internally located in the bottom of the right section 108.

The left section 106 is heated by reboiler 136 which is furnished with steam to supply the necessary heat. A $C_{5+}$ product stream is obtained from the bottom of the left section 106 in line 138. A $C_4$'s product is obtained from the bottom of the right section 108 in line 140.

The alternative embodiment of FIG. 8 shows a concentric dividing wall 142 as opposed to the straight dividing wall illustrated in FIG. 7. This has the advantage of avoiding circumferential thermal stresses in the column 100 due to temperature differences between the exterior section 106*a* and the interior section 108*a*.

EXAMPLE 1

As one example of the invention, the column 100 is designed for an ethylene plant producing 600 kt/a (1.32 billion pounds/year) of ethylene and compared to the separate low pressure depropanizer/debutanizer of the prior art. The conventional low pressure depropanizer has a diameter of 2.15 m (7 ft), a height of 37 m (121 ft), operates at 0.9 Mpa (30 psi), and uses 56 trays. Its reboiler operates at 72° C. (162° F.) and is heated with steam, while the reflux condenser is cooled with propylene refrigerant. The conventional debutanizer has a diameter of 1.6 m (6 ft 6 in), a height of 31 m (102 ft), operates at a pressure of 0.42 MPa (60 psia) and uses 40 trays. Its reboiler operates at 85° C. (185° F.) and is heated with steam, while the reflux condenser is cooled with cooling water.

In using the integrated column 100 of the present invention, the integrated column has a diameter of 2.2 m (7 ft 6 in), a height of 40 m (131 ft), operates at a pressure of 0.42 Mpa (60 psia) and uses 56 trays. Approximately 18 trays are used in the upper column portion 102. The high pressure depropanizer bottoms feed stream 38 is supplied to tray 37.

In the prior art low pressure depropanizer, the overhead temperature is 13° C. (55° F.) and the bottoms temperature is 71° C. (180° F.). In the conventional debutanizer, the overhead temperature is 35° C. (100° F.), while the bottoms temperature is 85° C. (185° F.). With the integration of the low pressure depropanizer and debutanizer into the single column 100 according to the present invention, the column 100 is operated with an overhead temperature of −12° C. (−54° F.), and the condenser duty increases from 5.4 MW (18.4 MMBtu/hr) to 7.7 MW (26.3 MMBtu/hr). The bottom stage temperature in the depropanizer section 108 of the lower column portion 104 is reduced to 40° C. (104° F.) and is reboiled by heat exchange with quench water instead of steam, saving 5.3 MW (18 MMBTU/hr) of heat. The reboiler 136 of the debutanizer continues to be heated with steam, but at a much lower rate, i.e. 1.9 MW (6.4 MMBUT/hr) compared to 3.6 MW (12.3 MMBtu/hr) for the conventional debutanizer reboiler. Thus, the steam savings more than offsets the increased condenser duty.

A comparison of the construction costs indicates that the new system saves significant capital costs compared to the conventional system of FIGS. 1–6. This example also shows that the use of a single distillation tower for debutanization and low pressure depropanization has the advantages of using one tower instead of two large towers, elimination of the debutanizer reflux condenser, reflux accumulator and pumps, and a much smaller debutanizer reboiler. The operation is likewise simpler since there are fewer pieces of equipment that need to be controlled.

The invention is described above in illustrative terms which are not intended to limit the invention. Many variations will become apparent to those skilled in the art in view of the foregoing description. It is intended that all such variations within the scope and spirit of the appended claims be embraced thereby.

What is claimed is:

1. An integrated low pressure depropanizer and debutanizer column for separating a feed stream comprising $C_3$'s, $C_4$'s and $C_{5+}$ into a $C_3$'s stream, a $C_4$'s stream and a $C_{5+}$ stream, comprising:

a single shell housing a refluxed upper portion and a lower portion, each of said portions comprising multiple vapor-liquid contacting elements;

a generally vertical wall partitioning the lower portion into a debutanizer section and a depropanizer stripper section;

a feed line for supplying at least one feed stream to at least one feed stage of the debutanizer section of the lower portion of the column, between a plurality of absorption stages in the debutanizer section above the feed stage and a plurality of stripping stages in the debutanizer section below the feed stage, for producing an overhead vapor stream from the debutanizer section consisting essentially of $C_3$'s and $C_4$'s and a bottoms stream consisting essentially of $C_5$ and heavier components;

a distribution pan at a lower end of the upper portion of the column for facilitating passage of vapors from the debutanizer and depropanizer stripper sections into the upper column portion, and for dividing liquid for passage from the upper portion of the column into an upper stage of the debutanizer section and into the depropanizer stripping section.

2. The integrated column of claim 1 wherein the debutanizer section comprises from 25 to 45 trays.

3. The integrated column of claim 1 wherein the upper and lower portions have the same cross-sectional diameter.

4. The integrated column of claim 1 including a reboiler for the debutanizer section heated with steam.

5. The integrated column of claim 1 including a reboiler for the depropanizer stripper section heated by quench water.

6. The integrated column of claim 1 comprising respective liquid lines from the distribution pan to the tops of the debutanizer section and the depropanizer stripper section.

7. The integrated column of claim 6 wherein the line from the distribution pan to the top of the debutanizer section includes a valve for controlling the amount of liquid supplied to the debutanizer section.

8. The integrated column of claim 1 having an operating pressure of from 1.5 to 12 bars (20 to 180 psia).

9. A process for separating a feed stream comprising $C_3$'s, $C_4$'s and $C_{5+}$ into a $C_3$'s stream, a $C_4$'s stream and a $C_{5+}$ stream, comprising:

supplying the feed stream to the at least one feed stage of the debutanizer section of the lower portion of the integrated column of claim 1;

passing overhead vapor from the debutanizer and depropanizer stripper sections through the distribution pan to the upper portion of the column;

refluxing the upper portion of the column with $C_3$'s and recovering $C_3$'s essentially free of $C_4$'s overhead from the upper portion of the column;

passing liquid from the distributor pan into an upper stage of the debutanizer section and into an upper stage of the depropanizer stripper section;

reboiling the debutanizer section and recovering a $C_{5+}$ bottoms product stream therefrom essentially free of $C_3$'s and $C_4$'s;

reboiling the depropanizer stripper section and recovering a $C_4$'s bottoms product stream therefrom essentially free of $C_3$'S and $C_{5+}$.

10. The process of claim 9 wherein the debutanizer section comprises from 25 to 40 trays and the upper and lower portions of the column have the same cross-sectional diameter.

11. The process of claim 9 including controlling the amount of liquid feed to the upper stage of the debutanizer section from the distribution pan.

12. The process of claim 9 wherein the integrated column is operated at a pressure from 1.5 to 12 bars (20 to 180 psia).

13. The process of claim 9 wherein the debutanizer section is reboiled with steam.

14. The process of claim 9 wherein the depropanizer stripper section is reboiled with quench water.

15. The process of claim 9 comprising controlling the amount of liquid passed from the distributor pan into the upper stage of the debutanizer section. section, and a distribution pan at a lower end of the upper portion of the column, the feed stage of the debutanizer section disposed between a plurality of absorption stages above the feed stage in the debutanizer section and a plurality of stripping stages in the debutanizer section below the feed stage;

means for passing overhead vapor from the debutanizer and depropanizer stripper sections through the distribution pan to the upper portion of the column;

means for refluxing the upper portion of the column with $C_3$'s and recovering $C_3$'s essentially free of $C_4$'s overhead from the upper portion of the column;

means for passing liquid from the distributor pan into an upper stage of the debutanizer section and into an upper stage of the depropanizer stripper section;

means for reboiling the debutanizer section and recovering a $C_5$+ bottoms product stream therefrom essentially free of $C_3$'s and $C_4$'s;

means for reboiling the depropanizer stripper section and recovering a $C_4$'s bottoms product stream therefrom essentially free of $C_3$'s and $C_{5+}$.

16. Apparatus for separating a feed stream comprising $C_3$'s, $C_4$'s and $C_{5+}$ into a $C_3$'s stream, a $C_4$'s stream and a $C_{5+}$ stream, comprising:

means for supplying the feed stream to at least one feed stage of a debutanizer section of a lower portion of an integrated column comprising a single shell housing a refluxed upper portion and a lower portion, each of said portions comprising multiple vapor-liquid contacting elements, a generally vertical wall partitioning the lower portion into the debutanizer section and a depropanizer stripper section.

\* \* \* \* \*